United States Patent [19]

Weissman

[11] Patent Number: 4,820,159

[45] Date of Patent: Apr. 11, 1989

[54] DENTAL POST AND CORE ASSEMBLY

[75] Inventor: Bernard Weissman, New York, N.Y.

[73] Assignee: IPCO Corporation, White Plains, N.Y.

[21] Appl. No.: 76,639

[22] Filed: Jul. 23, 1987

[51] Int. Cl.$^4$ ................................................. A61C 5/04
[52] U.S. Cl. ..................................... 433/225; 433/49; 433/215; 433/165
[58] Field of Search ...................... 433/225, 221, 201.1, 433/220, 175, 191

[56] References Cited

U.S. PATENT DOCUMENTS

| | | | |
|---|---|---|---|
| 2,438,725 | 3/1948 | Tamarin | 433/225 |
| 3,952,415 | 4/1976 | Samuel et al. | 433/49 |
| 4,187,611 | 2/1980 | Chan | 433/225 |
| 4,260,383 | 4/1981 | Weissman | 433/225 |
| 4,473,353 | 9/1984 | Greggs | 433/215 |
| 4,708,655 | 11/1987 | Weissman | 433/225 |
| 4,722,687 | 2/1988 | Scortecci | 433/165 |

Primary Examiner—Larry Jones
Attorney, Agent, or Firm—Helfgott & Karas

[57] ABSTRACT

A dental core and post assembly for use in the formation of a dental core for the restoration of a tooth structure. The dental post assembly includes a support structure for positioning into a prepared tooth root to be restored. At least one leg depends from the support structure for insertion into an ancillary bore predrilled into the root adjacent a central bore predrilled through a canal in the tooth root. An axial aperture through the support structure permits a pin to be adjustably inserted through the axial aperture and into the central bore until it is seated in the central bore. The leg is contiguous with the pin. In one form the invention provides a burnout core and post for the direct technique of forming a post and core system. In another form, the invention provides an impression post for use in connection with the formation of an impression in the indirect technique of forming the core and post system.

25 Claims, 6 Drawing Sheets

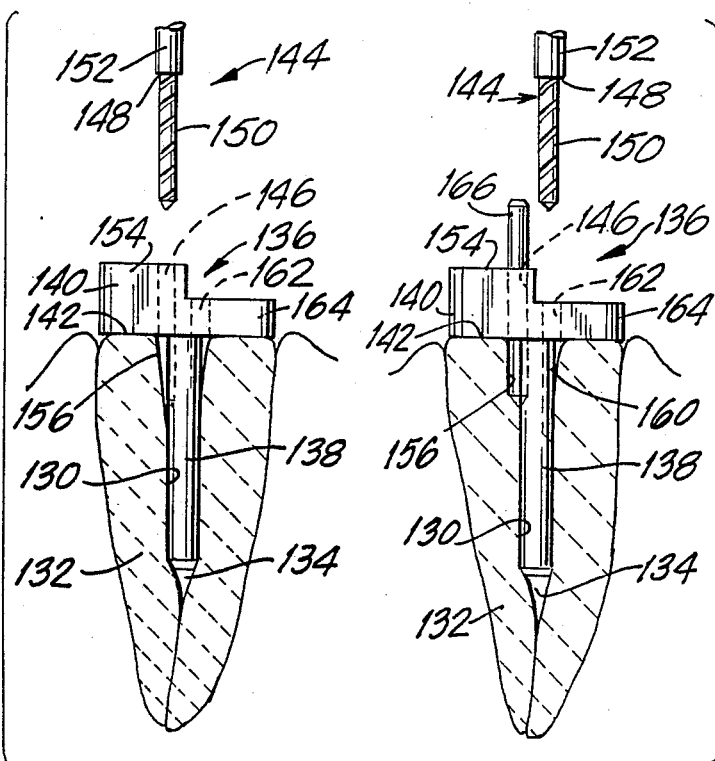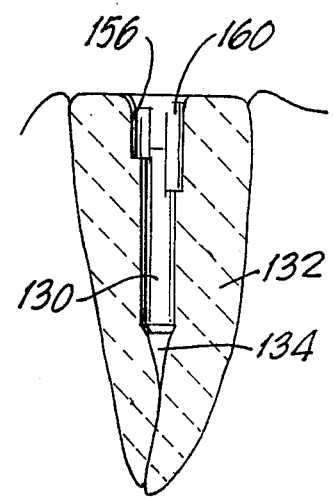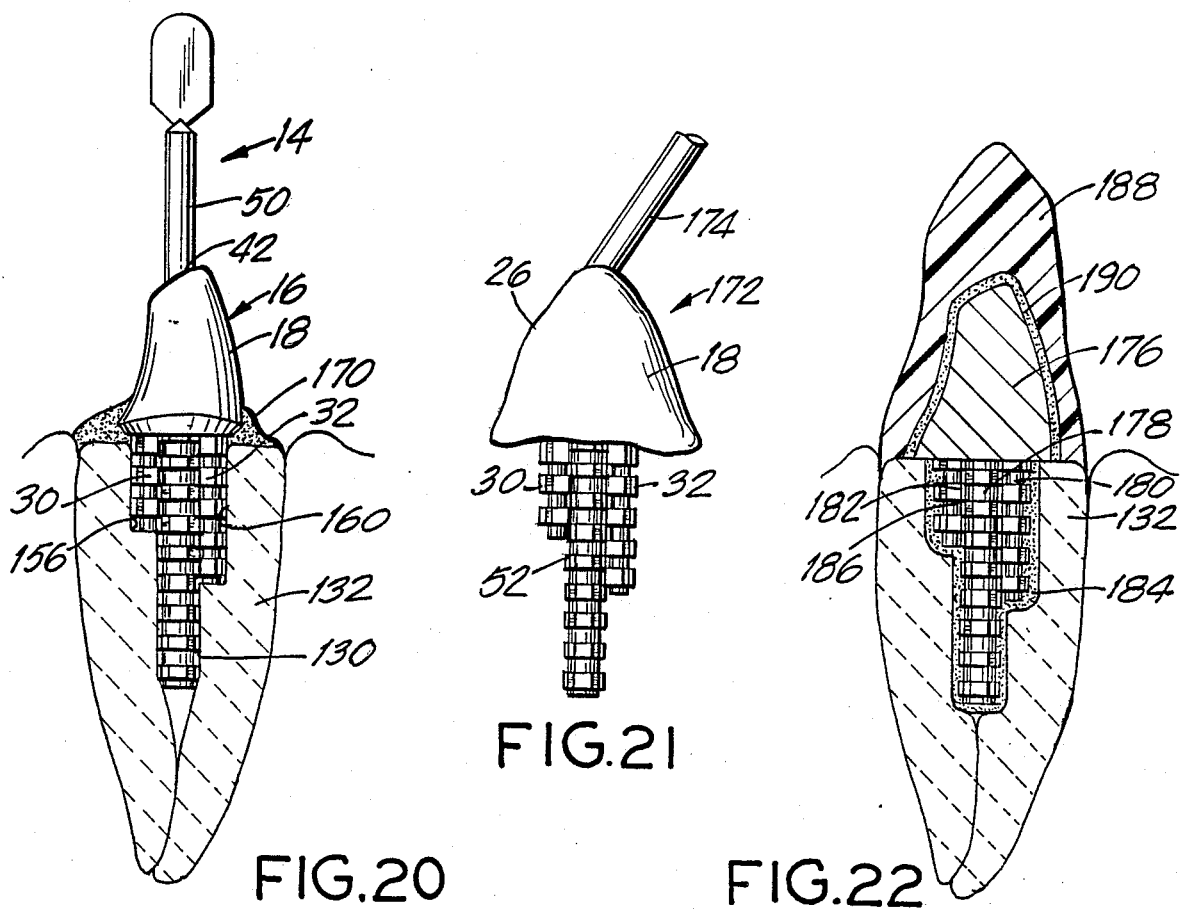

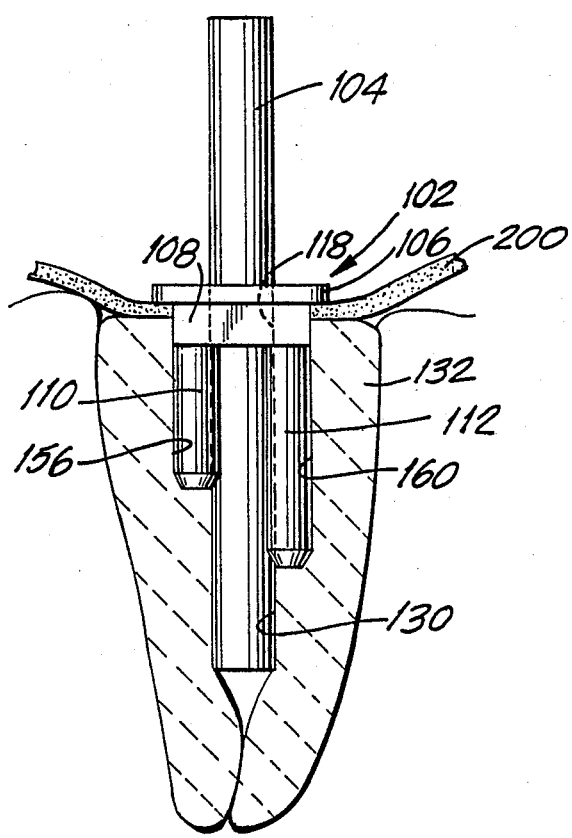
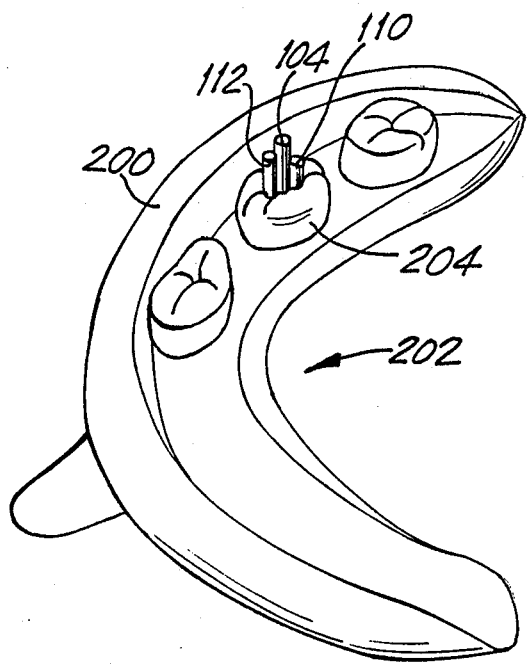
FIG.23　　　　　　　FIG.24
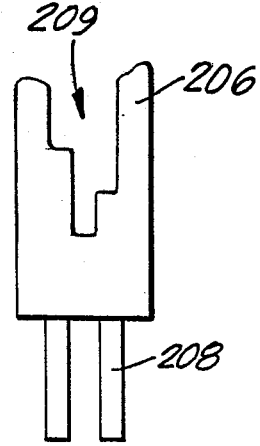
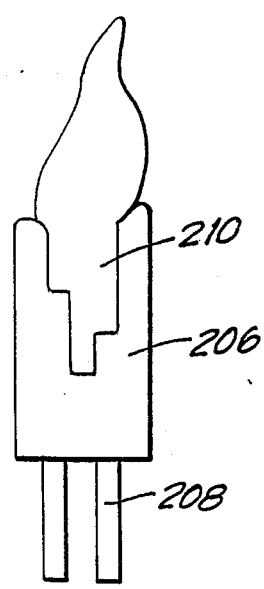
FIG.25　　　　　　　FIG.26

DENTAL POST AND CORE ASSEMBLY

BACKGROUND OF THE INVENTION

This invention relates to dental apparatus, and more particularly to dental post and core assemblies for use in the formation of a dental core as part of the restoration of a tooth structure, and specifically to devices commonly known as post and core systems as well as impression transfer posts.

In the restoration of damaged teeth, one technique that is frequently used is to prepare the tooth understructure or tooth root, and build upon it a superstructure including a core anchored with a post and upon it a crown. The technique generally includes preparing the tooth root through various procedures including endodontic treatment. The canal is then predrilled to form an enlarged bore coaxial with the root canal. A post is inserted into the pre-drilled bore and a core is fabricated and attached to it creating a retentive foundation. A crown is then fabricated as the final part of the restoration.

Various techniques have been established for forming the post and core. One method is referred to as the direct technique a procedure whereby the dentist at the chairside performs the necessary steps in sequence to prepare a pattern for casting the object. This involves the use of a plastic post which is inserted into the pre-drilled bore in the tooth root. Using appropriate wax or resin, a core is fabricated directly on the tooth structure. The core with the connected post is then sprued and invested in a conventional manner, and is cast using a typical "lost wax process". The cast post and core inserted and cemented in the dentition, becomes the foundation for the restoration of choice.

Using an indirect method, where the dentist preparing the tooth in every detail makes an impression of the dentition and the dental technologist performs the necessary tasks, in sequence, on a dental cast obtained from the impression and delivers to the dentist the final product, an impression is formed of the tooth root and surrounding area. The impression is then sent to a laboratory where technicians using standard procedures initially prepare a dental model from the impression. On the dental model, a core pattern is fabricated by conventional wax method and/or using self curing resin Appropriate posts are inserted into the dental model as part of the fabricated core. The fabricated core and post is sprued and invested and used to form the final cast core. This is inserted into the actual dentition and the final restoration of choice is formed.

In many cases, especially where the tooth is rather large, in addition to the central post, retention pins are utilized. Such pins provide additional securement of the core onto the tooth root. The use of the pins also prevents rotation of the core with respect to the tooth root.

One problem that is faced using these various known techniques is that the particular shape of the canal, and especially the mouth of the canal, is not regularly accommodated by the single central bore. Typically, the upper end of the canal is outwardly flared and often represents an oval or elliptical shape in cross section. The placement of the single cylindrical post to fit in the rather large mouth of the canal would not be feasible since the lower portion of the canal and the root are much narrower. Thus utilizing a larger cylindrical post would cause the weakening or side perforation of the root.

The problem of the wider mouth area of the canal structure has been addressed in U.S. Pat. No. 4,600,392, issued to the same inventor and assignee of the present invention. In that patent, there is described a dental post which is contoured to have ribs at the side of a central rod. In that patent, the post is utilized in a technique whereby the post is directly cemented in the bore and the core is mechanically secured to the post by a locking arrangement. The bore is initially formed as a central bore and subsequently, using jigs, ancillary bores on either side are formed in communication with the central bore but accommodating the side ribs on the post. One of the ribs is shorter than the other to distribute forces and to add resistance to them in a most advantageous manner.

While such post with side ribs has been used to directly connect a core, the problem of the wide mouth at the upper end of the canal has not been addressed in connection with casting of post and core systems.

An additional problem with both the direct and indirect methods is that when the initial central bore is formed, the depth of the bore is not accurately known. As a result, a post that is inserted into the central bore may not seat properly to the bottom of the bore.

Accordingly, there is need of an improved type of dental post assembly for use in connection with both the direct and the indirect techniques for forming core and post castings.

SUMMARY OF THE INVENTION

It is accordingly an object of the present invention to provide an improved dental post assembly for use in the formation of a dental core in the restoration of a tooth structure.

A further object of the present invention is to provide an improved burnout core and post which can be utilized in the direct technique formation of a cast core.

Yet a another object of the present invention is to provide an improved impression transfer post which can be utilized in the direct technique for the formation of a cast core and post.

Yet a further object of the present invention is to provide an improved dental post assembly for casting post and core systems and which accommodates for the oval shaped opening at the upper end of a canal in a tooth root.

Still a further object of the present invention is to provide an improved dental post assembly utilizing contiguous pins adjacent to a central post for approximating the oval shape at the entry to the canal in a tooth root.

Still another object of the present invention is to provide a dental post assembly system including a pair of adjacent legs for fitting into the oval shaped region of the canal in a tooth root and a sliding central post which can fit into the bottom of a central bore in the tooth root.

A further object of the present invention is to provide a prefabricated post and core system with an adjustable post whose depth can be adjusted to accommodate the bore depth to achieve proper seating of the post.

Yet a further object of the present invention is to provide a method for casting core and post systems where a central bore and a pair of ancillary bores are drilled into the tooth root to accommodate for a dental post assembly having a pair of side legs contiguous with an adjustable central post for fitting into the wide oval shaped mouth of the tooth root.

Briefly, in accordance with the present invention, there is provided a dental post assembly for use in the formation of a dental core in the restoration of a tooth structure. The dental post assembly includes a support structure for positioning onto a prepared tooth root which is to be restored. At least one leg depends from the support structure for insertion into an ancillary bore predrilled into the tooth root adjacent a central bore. The central bore is also pre-drilled and extends through the main canal in the tooth root. An axial aperture is provided through the support structure. A pin is provided which is adjustably insertable through the axial aperture in the support structure and can extend into the central bore until it is seated therein. The legs are contiguous with the pin.

In an embodiment of the invention, a pair of legs are provided which depend from the support structure and which are in diametric opposition to each other with respect to the pin. The legs are both contiguous to the pin.

In an embodiment, the support structure is a preformed core and the legs and the pin are annularly grooved. The dental post assembly can then be used as a burnout core and post system in the direct technique of casting posts and cores.

In an another embodiment, the support structure is a flat platform and both the legs and the central pin are smooth. The dental post assembly can then be used as an impression transfer post in the formation of an impression for the indirect technique of forming a post and core cast system.

The present invention also contemplates a method of fabricated cast cores and posts for dental restoration of a tooth structure. The method includes drilling a central bore into the main canal of the tooth root. Using a jig, at least one ancillary bore is formed contiguous with the central bore and of a fixed depth. A pre-fabricated dental assembly is utilized which includes a support structure having a depending leg whose length fits into the depth of the ancillary bore. A central pin adjustably fits through an axial aperture formed in the support structure and is extended downwardly until it bottoms into the central bore.

In the indirect method, suitable impression material would be utilized to form an impression which can then be sent to a laboratory wherein the dental post assembly of the present invention would be formed as part of the impression to define the central and ancillary bores in the model, substantially formed with use of the impression material. In the direct method, the present invention would be used as a prefabricated core and post of suitable resin, plastic or wax and additional material would be used to fill in and shape the core to a desired shape. It would then be sprued and invested to form a cast metal post and core system for insertion and cementation into the tooth structure.

The aforementioned objects, features and advantages of the present invention will, in part, be pointed out with particularity, and will, in part, become obvious from the following more detailed description of the invention taken in conjunction with the accompanying drawing, which forms an integral part thereof.

BRIEF DESCRIPTION OF THE DRAWINGS

In the Figures:

FIG. 17 shows a cross sectional view through a tooth root showing the use of a dental jig in the formation of an ancillary bore contiguous with a central bore;

FIG. 18 is a view similar to that shown in FIG. 17 but showing yet a further step and specifically in a formation of a second ancillary bore;

FIG. 19 is a view similar to that shown in FIG. 18, but showing and completed central bore with the two ancillary bores;

FIG. 20 is a view similar to that shown in FIG. 17, and showing the insertion of the anterior burnout core and post of FIG. 1 into the prepared tooth root;

FIG. 21 shows the completed burnout core and post suitably shaped with resin sprued and invested ready for casting of the metal post and core system;

FIG. 22 shows the completed tooth with the cast core and post cemented into the tooth root and with the final restoration in place;

FIG. 23 shows the use of the impression post of FIG. 12 inserted into a tooth root prepared in accordance with FIG. 19;

FIG. 24 is a top view of an impression tray in which the impression post of the present invention has been included;

FIG. 25 is a side view of a die formed as part of a working model fabricated from the impression tray of FIG. 24, and FIG. 26 shows the cast core formed using conventional casting techniques to form a post and core system and which is fit into the die.

In the various figures of the drawing, like reference characters designate like parts.

DESCRIPTION OF THE PREFERRED EMBODIMENT

Figure 1:
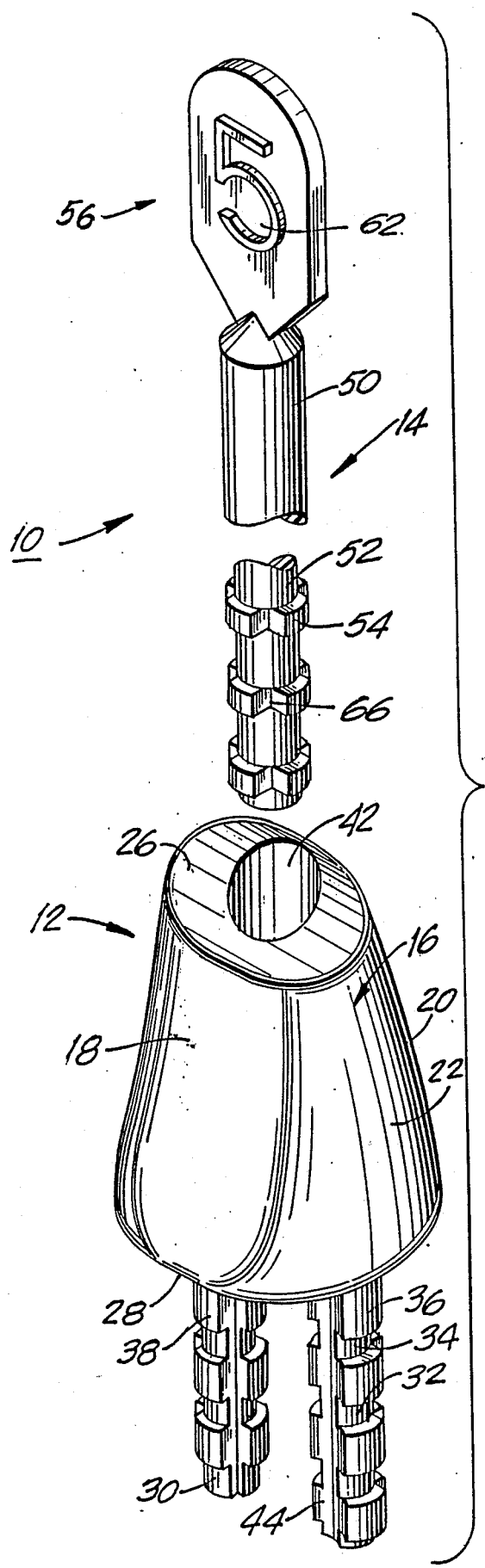
FIG. 1 is a perspective exploded view of the dental post assembly of the present invention in the form of an anterior burnout core and post.

Referring now to FIGS. 1, 7, 8 and 9, there is generally shown a dental post assembly 10 in the form an anterior burnout core and post 14. The anterior core includes a body portion 16 whose configuration is shaped to generally conform to typical prefabricated cores for use on anterior teeth. The body portion includes arcuate front and back walls 18, 20 opposing side walls 22, 24, a top wall 26, and bottom wall 28. Depending from the bottom wall 28 are a pair of legs 30, 32, with leg 30 being shorter than leg 32.

Each of the legs 30, 32 are substantially cylindrical in cross sectional configuration. They include a cylindrical body portion 34 and spaced apart annular projecting rings 36. Four rings are provided on the leg 32 and because of the shorter length, 3 rings are provided on the leg 30. As will hereinafter be described, the rings provide greater retention of the ultimate cast core and post into the pre-drilled bores in the prepared tooth.

Figure 6:
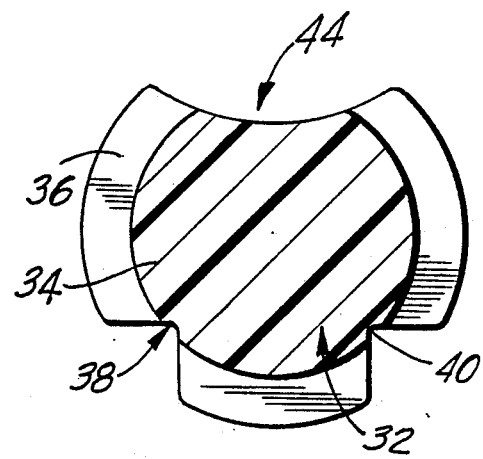
FIG. 6 is a cross sectional view taken through line 6—6 of FIG. 7.
Figure 7:
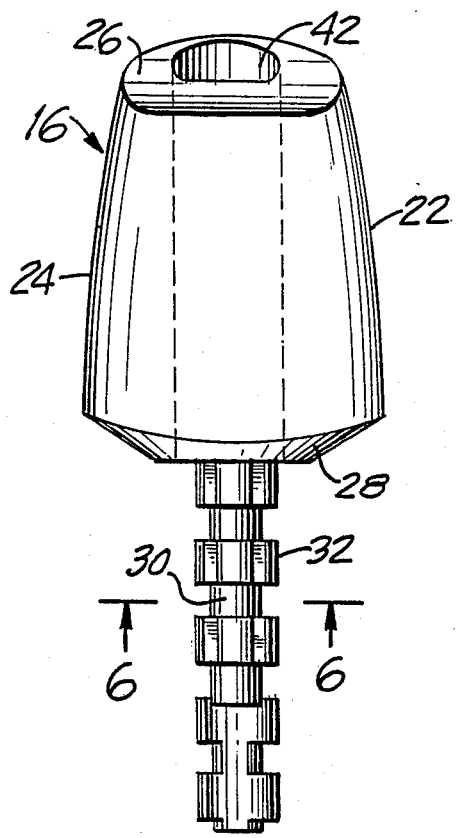
FIG. 7 is a front elevational view of the anterior burnout core shown in FIG. 1.
Figure 8:
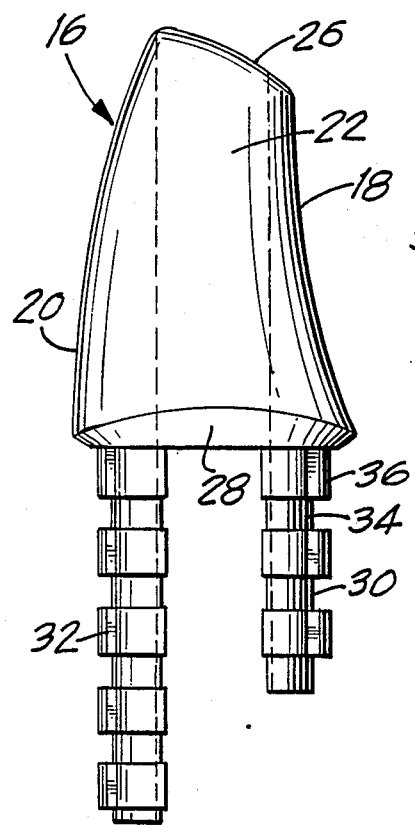
FIG. 8 is a side view thereof.

As best seen in FIG. 6, which is taken as a cross section along FIG. 7, a pair of opposing elongated V-shaped vent channels 38, 40 are provided along the entire length of the legs 30 and 32. The vents aid in seating of the legs and the ultimate cast post and core.

Figure 9:
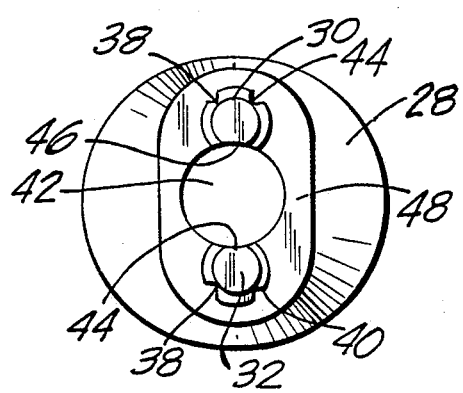
FIG. 9 is a bottom view thereof.

An axial aperture 42 is formed through the entire length of the body portion 16. The two legs 30, 32 are contiguous to the central aperture 42 such that the aperture intersects portions of the legs 30, 32 to form the arcuate cutouts 44, 46, as is best seen in FIG. 9. As best seen n FIG. 9, the opposing legs are seated on an oval flat base 48 from which the bottom wall 28 tapers upwardly to form side undercuts, as best seen in FIG. 7.

Figure 11:
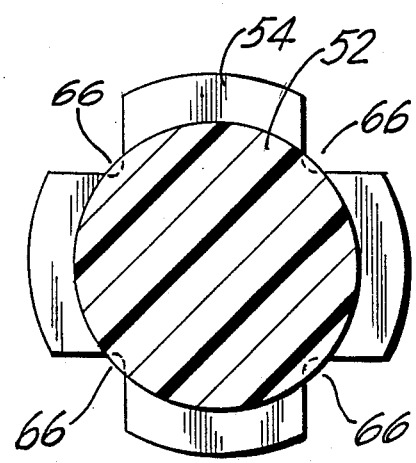
FIG. 11 is a cross sectional view taken along lines 11—11 of FIG. 10.
Figure 10:
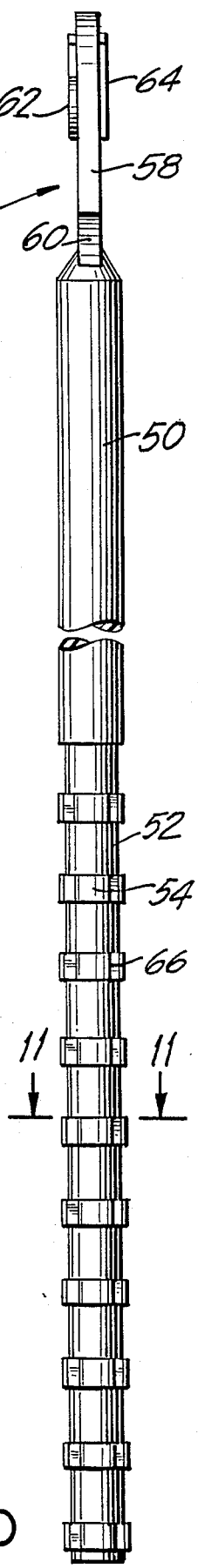
FIG. 10 is a side view of the burnout post shown in FIG. 1.

Referring now to FIGS. 1, 10 and 11, the burnout post 14 is shown to be formed of a substantially cylindrical elongated body portion 50. At the upper end, the body portion 50 has a smooth periphery. At a lower portion, there is provided reduced section portions 52 separated by annular projecting rings 54 which are spaced along the bottom length thereof. The purpose of the annular rings as in connection with the legs 30, 32 heretofore described, aids in providing additional retention of both the burnout post in the bore as well as the cast core and post when it is cemented in the bore in the prepared tooth.

At the upper end of the cylindrical portion 50 is provided head 56 including a flattened tang portion 58 projecting from a neck portion 60. Suitable indicia 62, 64 can be provided to identify the size of the particular burnout post. It should be appreciated, that the size of the post would correspond to the size of the predrilled hole formed in the tooth and likewise would correspondingly cause the axial aperture 42 in the core to be a corresponding size. In fact, an entire series of sized anterior core and burnout posts can be provided. Furthermore, these can be color coded so that the entire color of the post and core will correspondingly match to a size of the drill being utilized to drill the bore which can also be similarly color coded.

As is best seen in FIG. 11, a plurality of axially extending V-shaped channels 66 are formed at 4 locations equally spaced about the periphery of the burnout post. The notches extend into the annular projecting rings 54 and slightly penetrate the main cylindrical post at the center 52. These channels serve as vents to permit excess cement to escape during installation and provide for full seating of the ultimate core and post.

As is best noted in FIG. 1, the burnout post can be inserted into the axial aperture 42 provided in the body 16 of the core 12. It is of sufficient length so that the lower portion can be extended to depend further downward than the two legs 30, 32 depending from the core portion.

Although the post is shown as axially sliding in the aperture 42, the post can be threaded and can threadingly engage a threaded aperture in the core to be axially adjustable.

Although the core portion heretofore described was particularly suited for anterior teeth, as can best be seen in FIGS. 2, 3, 4 and 5, a different shaped core can also be provided which is best suited for posterior teeth.

The posterior core is shown generally at 70 and includes a body portion 72 with a pair of depending legs 74, 76. The body portion comprises front and back walls 78, 80 which are outwardly flared and interconnected by side walls 82, 84. The top wall 85 includes a slight downward depression toward the center. The bottom wall 86 is downwardly flared to produce the edge undercuts and terminates in an oval base platform 88 from which depends the legs 75, 76. An aperture 89 extends entirely through the core portion 70.

Of the legs, leg 76 is shorter than leg 74. Each of the legs include the cylindrical body portion 90 with the spaced apart annular projecting rings 92. A pair of V-shaped vent channels 94 are provided on each of the legs. The center aperture 89 is such as to extend downwardly through the opposing legs 74, 76 to cause arcuate cutouts 96, 98 from the legs 74, 76 where they are contiguous with the center aperture 89.

Figure 2:
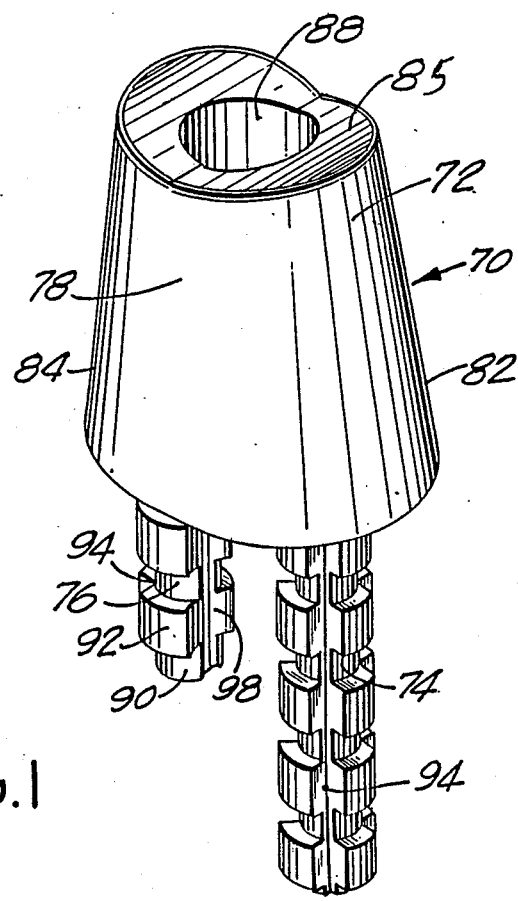
FIG. 2 is a perspective view of another embodiment of the present invention showing the posterior burnout core which would be used with a burnout post similar to that shown in FIG. 1.
Figure 3:
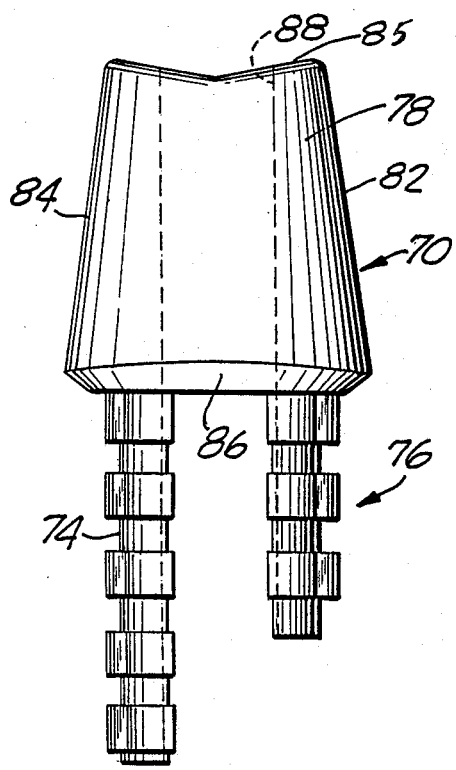
FIG. 3 is a front view of the posterior burnout core of FIG. 2.
Figure 4:
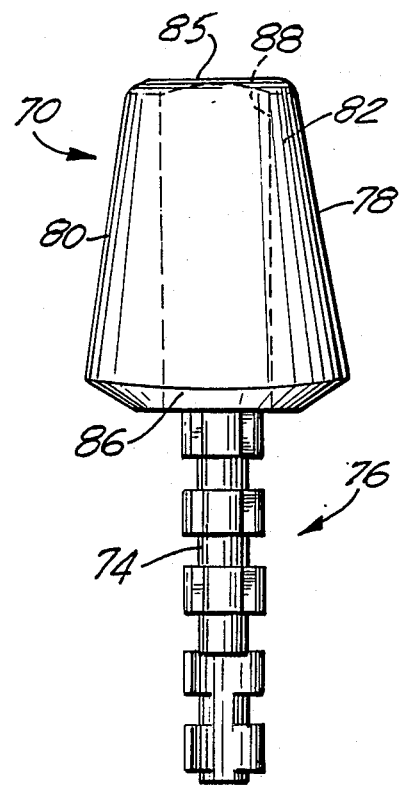
FIG. 4 is a side view thereof.
Figure 5:
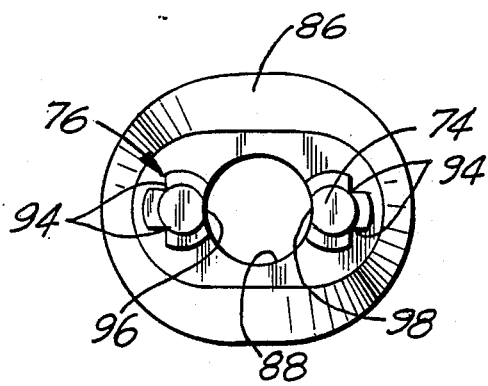
FIG. 5 is a bottom end view thereof.

Although not shown specifically in FIG. 2, the same burnout post 14 shown in FIG. 1 would also be utilized in connection with the posterior core shown in FIG. 2. Again, coordinated colors and sizes can be provided.

Although two particular shapes of cores were shown, it should be appreciated that other shapes could likewise be utilized as in needed. In each case, a predetermined core is provided which is shaped generally to accommodate the basic core structure needed. As will hereinafter be described, suitable resin, plastic, wax, or the like, will be used to produce the final shaped core and post for casting the metal core and post to be cemented and become part of the reconstructed tooth.

Referring now to FIGS. 12, 13, 14, 15 and 16, another embodiment of the present invention will be shown, specifically, there is generally shown an impression post 100 including a body portion 102 and a cylindrical pin portion 104. The body portion includes an upper platform 106 from which depends a pedestal 108. Both the body portion 106 and the pedestal portion 108 are of substantial rectangular configuration with rounded corners with the pedestal portion 108 having a somewhat reduced peripheral size than the body portion 106 so as to provide an overhang of the platform 106. Depending from the pedestal 108 are a pair of legs 110, 112 with the leg 110 shorter than the leg 112. Both legs are smooth with a slight champher at the lower tip 114, 116. Both legs 110 and 112 are peripherally smooth and cylindrical.

A central aperture 114 is provided through the platform 116 and the pedestal 108. However, as can best be seen in FIG. 16, the aperture 118 extends downwardly so as to provide a pair of opposing cutouts 120, 122 in the sections of the side legs 110, 113 contiguous with the center aperture 118. The cylindrical post 104 having a smooth periphery, can easily fit into the aperture 118. The post 104 is of a size sufficient so that it can extend downwardly below the legs 110, 112.

The use of the dental post assembly of the present invention will best be described in connection with the rest of the figures. As is well known, in providing a post and core for use in a dental restoration, either a direct or indirect technique can be utilized. In the direct technique, initially, the tooth root is prepared by providing completion of the endodontic treatment whereupon the apical section of the canal is sealed. The canal is then drilled to form a central bore coaxial with the canal. Typically, successively larger drills are utilized to enlarge the canal to the desired width and a desired depth. However, generally, the exact depth is often not known.

Referring now to FIG. 17, after the central bore 130 has been formed in the tooth stub 132 which central bore corresponds axially with the apical canal 134, additional ancillary bores are drilled. A drill jig 136 is mounted on top of the tooth root 132 with the shaft 138 of the drill jig being inserted in the central bore 130 and the lower surface of the head block 140 being placed on the upper surface 142 of the tooth root 132. A drill 144 is inserted into an aperture 146 of the drill block and is rotated until its shoulder portion 148, between the bit 150 and the shaft 152, reaches the top surface of a thicker portion 154 of the head block 140. In this manner, a short aperture or bore 156 will be drilled into the canal wall of the tooth root 132 in communication with the main bore 130. It should be noted, that the drill 144 being used for the ancillary bore 156 may be of smaller diameter size than the bit utilized to form the central bore.

With the same drill 144, a second ancillary bore 160 will now be drilled into the canal wall, also in communication with the center bore 130. This can best be seen in FIG. 18. Because of the stepped arrangement of the head block 140, the same drill bit 144 can be utilized to drill the two ancillary bores 156, 160 whereby the bore 160 will result in a deeper aperture in the tooth root 132. As indicated in FIG. 18, the drill 144 is inserted into the other aperture 162, and the shoulder portion 148 of the drill 144 will abut the top surface of the thinner portion 164 to stop the depth of the drilling of the ancillary bore 160. Preferably before drilling the ancillary bore 160 a pin 166 is inserted through the aperture 146 into the ancillary bore 156 to maintain the drill jig 136 in a fixed position to ensure the correct relationship between the ancillary bores 156 and 160.

As shown in FIG. 19, after removal of the dental jig 136, a resulting bore hole is provided in the tooth root 132 which includes a substantially cylindrical central bore 130 and including an ancillary bore of shorter depth 156 on one side and an ancillary bore 160 of deeper penetration on the diametrically opposing side. The total bore at the upper end will approximate an oval or elliptical configuration which will be in close conformity to the actual shape at the mouth of the canal 134 of the tooth root 132.

With the tooth root 132 thus configured, the burnout core and post of FIG. 1 or 2 could be utilized. By way of example, FIG. 20 shows the insertion of the anterior core and post of FIG. 1. The larger leg 32 is shown inserted into the deep bore 160. The shorter leg 30 is inserted into the shorter bore 156. Since the depth of the ancillary bores has been accurately measured, and such measurement corresponds to the actual length of the legs, the bottom of the legs 30, 32, will suitably seat at the lower ends of the two ancillary bores. The body portion 18 will sit slightly upwardly above the tooth surface and especially with the peripheral undercut at the bottom of the body portion of the core, there will be some space available. The central post is then inserted into the aperture 42 at the axial center of the body portion of the core and is pushed downwardly until it seats at the bottom of the central larger bore 130. Since the central post is adjustable, even though the exact depth of the central bore is not known, the central post can be extended downwardly until it seats at the bottom of the bore. At this point, all three depending portions, namely the two legs and the central post, will all be seated fully into the respective bores that were pre-drilled.

Suitable resin 170 is then placed at the bottom, sides, and appropriately other positions around the prefabricated core. The resin is packed around the core 16 and is allowed to set. The core and post is then removed from the tooth. As shown in FIG. 21, the pattern resulting is shown generally at 172, and includes the upper core portion 18, which is now suitably shaped to the desired core which will be utilized for the actual reconstruction. The opposing legs 30, 32 are now incorporated within the structure as is the central post 52. The upper end of the post above the top surface 26 can be cut or utilized as a sprue. The pattern is sprued 174, and invested in a conventional manner. The core and post is then cast with appropriately formulated metal materials. After the core and post is cast, it is checked for fit and accuracy and then is inserted into the tooth structure, as shown in FIG. 22. The resulting core 176 now includes integrally the central post 178, and the side legs 180, 182. All of these will fit accurately into the pre-drilled bore. Appropriate cement 184 is used to seat the legs into the predrilled bores. The annular rings 186 which are now cast directly into the core and post system will aid in the retention of the core and post in the bore. A final restoration or crown of choice 188 is then applied and attached by suitable adhesive 190.

It will be appreciated that because of the presence of three legs, a better fit is provided since the top of the legs correspond to the oval wide mouth shape at the mouth of the canal. Likewise, because of the presence of the side legs, better retention is provided. In fact, in many cases, there will be no need for additional pins because of the presence of the additional legs as part of the core which is cast. Furthermore, since there is not just a central post but there are side legs, appropriate orientation is aided in the insertion of the core and prevention of rotation in the tooth root is provided.

Figure 12:
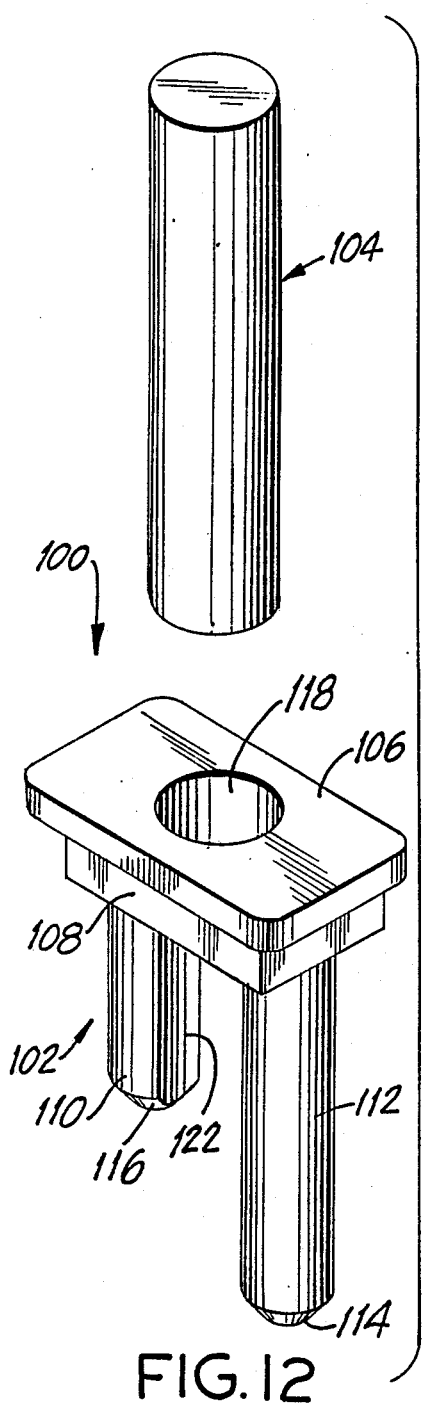
FIG. 12 is a perspective exploded view of another embodiment of the dental post assembly of the present invention in the form of an impression transfer post.
Figure 14:
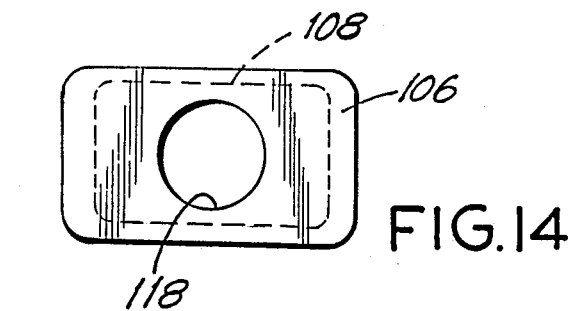
FIG. 14 is a top view thereof.
Figure 13:
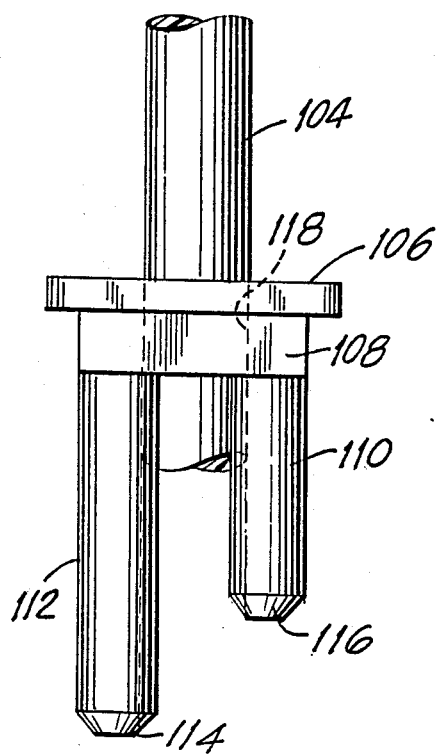
FIG. 13 is an elevational view of the assembled impression post of FIG. 12.
Figure 16:
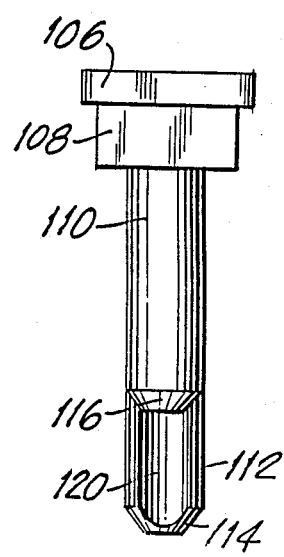
FIG. 16 is a side view thereof.
Figure 15:
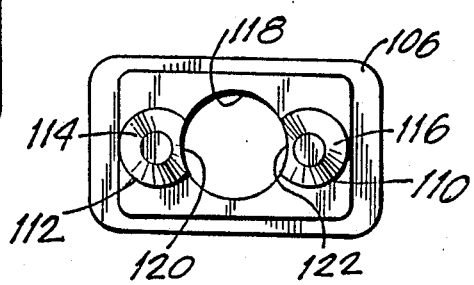
FIG. 15 is a bottom view thereof.

In utilizing the impression post shown in FIG. 12, the basic type of preparation of the tooth root would again be provided, as was shown in FIGS. 17, 18 and 19. At this point, however, the body structure 102 of FIG. 12 will be inserted as is shown in FIG. 23. The leg 110 would fit into the shorter ancillary bore 156. The longer leg 113 would fit into the deeper ancillary bore 160. The upper platform 106 would be spaced above the surface of the tooth stub 132 with the pedestal 108 sitting on the surface or adjacent thereto. The two legs 110, 112 would be seated fully at the bottom of their bores. The central post 104 would then be inserted through the aperture 118 and pushed downwardly until it seats in the bottom of the central bore 130.

At this point, as is well known, suitable impression material 200 would be placed under the platform 106, around the pedestal and in all other areas, to conform to the surface of the tooth area.

As shown in FIG. 24, a suitable impression 202 would be formed having the impression material 200 and carrying the form of the various teeth including the tooth 204 which is being treated. It is noted, that the central post 104, with the side legs 110, 112 project upwardly through the impression material defining the bore structure in the tooth root. The smooth impression post and ancillary pins are removed and the performed vented and grooved plastic post and core are used to form and shape and make ready for casting the metal post and core.

Using standard laboratory procedures, a suitable working model would be formed from the impression with a cast die removable section 206, as shown in FIG. 25 formed representing the tooth. Appropriate legs 208 would be provided to reset the removable die section into the cast. The bore structure 209 provided in the die cast represents the bores predrilled including the central bore and the ancillary side bores.

As shown in FIG. 26, an appropriate core and post 201 would be prepared using the procedures described in FIGS. 20, 21, 22. The cast core and post would then be fitted first into the removable die and subsequently in the actual tooth. It would then be cemented into the tooth and a final restoration provided to cause a result similar to that shown in FIG. 22.

In addition to forming the present invention out of plastic and used as a burnout core and post, the prefabricated core and post could be made out of metal. If the top surface of the tooth is flat and perpendicular to the central bore, the prefabricated core and adjustable post can be made of metal and used as the final adjustable core. In this case it might be preferable to make the post threaded into the core. The core would then be placed on the flat top surface of the tooth root, the side legs inserted into the ancillary bores, and the central post threaded through the core until it seats in the central bore. The core and post would then be cemented in place. At some point the top of the post would be cut off. The crown would then be fabricated over the core.

There has been disclosed heretofore the best embodiment of the invention presently contemplated. However, it is to he understood that various changes and modifications may be made thereto without departing from the spirit of the invention.

I claim:

1. A dental post and core assembly for use in the formation of a dental restoration, comprising a support structure for positioning onto a prepared tooth root to be restored, at least one leg depending from the support structure for insertion into an ancillary bore pre-drilled into the tooth root adjacent a central bore pre-drilled through a canal in the tooth root, an axial aperture through the center of the support structure, and a pin matingly fitting into and adjustably insertable through the axial aperture to adjust its length dependent from the support structure and into the central bore until seated therein, said leg being contiguous with the pin.

2. A dental post assembly as in claim 1, and comprising a pair of legs depending from said support structure in diametric opposition with respect to said pin and contiguous therewith for respective insertion in pre-drilled ancillary bores diametrically opposed with respect to the central bore in the tooth root.

3. A dental post assembly as in claim 2, wherein one leg is shorter than the other leg, and wherein said pin is adjustable in the axial aperture to a depth greater than either leg.

4. A dental post assembly as in claim 2, wherein the legs and the pin are respectively substantially circular in cross section, said legs having arcuate cutouts facing the pin to accommodate the intersecting passage of the pin therethrough.

5. A dental post assembly as in claim 1, wherein said support structure comprises a preformed core configuration whereby said dental post assembly can be used as a burnout core and post.

6. A dental post assembly as in claim 5, wherein said leg and pin are of substantially cylindrical body configuration, and comprising annular retention means around the periphery of each of the leg and pin.

7. A dental post assembly as in claim 6, wherein the retention means comprise axially spaced apart annular ribs projecting therefrom.

8. A dental post assembly as in claim 7, and comprising vent slots along the length of each of the leg and pin.

9. A dental post assembly as in claim 8, and wherein said vent slots are axially extending, V-shaped notches extending into said ribs.

10. A dental post assembly as in claim 9, and wherein said notches extend into the cylindrical body portion of the leg and pin.

11. A dental post assembly as in claim 6, and wherein said retention means is only on a lower part of said pin.

12. A dental post assembly as in claim 6, and comprising an enlarged head at the upper distal end of the pin.

13. A dental post assembly as in claim 12, and comprising an indicia on said enlarged head identifying the size of the pin.

14. A dental post assembly as in claim 1, wherein said support structure comprises a substantially flat platform whereby said dental post assembly can be used as an impression post.

15. A dental post assembly as in claim 14, wherein said leg and pin are substantially cylindrical in shape with a smooth outer periphery.

16. A dental post assembly as in claim 14, and further comprising a pedestal beneath said flat platform for raising said platform above the surface of the tooth root to accommodate impression material inserted therebeneath.

17. A dental burnout core and post assembly, comprising a prefabricated core, at least one pin axially depending therefrom, an axial aperture through said core, a post adjustably extending through said aperture in said core, said post and pin being receivable within a main bore and a laterally adjacent ancillary bore in a prepared tooth root, and wherein said pin and post are contiguous to each other.

18. A dental burnout core and post assembly as in claim 17, and comprising a pair of said depending pins diametrically opposed to each other with respect to said pins, both pins being contiguous with the post to define a substantially oval configuration.

19. A dental burnout core and post assembly as in claim 18, and wherein said post and pins comprise annular grooves around the periphery thereof, and vent channels axially therealong.

20. An impression post comprising, a substantially flat platform, at least one leg depending therefrom, an axial aperture through said platform, a post adjustably extending through said aperture, said post and pin being receivable within a main bore and a laterally adjacent bore in a prepared tooth root, and wherein said pin and post are contiguous to each other.

21. An impression post as in claim 20, and comprising a pair of said depending pins diametrically opposed to each other with respect to said post, both pins being contiguous with said post to define a substantially oval configuration.

22. An impression post as in claim 20, and wherein said pin and post are substantially cylindrical in shape with a smooth outer periphery.

23. A method of fabricating cast cores and posts for dental restoration of a tooth structure using a prefabricated assembly including a support structure having a depending leg and a post axially adjustable through an aperture in said support structure, the post and leg being contiguous, the method comprising:
- drilling a central bore into a canal of the tooth root;
- drilling at least one ancillary bore contiguous with the central bore and of a fixed depth corresponding to the length of the leg;
- inserting the prefabricated dental post assembly into the prepared tooth root with the leg seated in the ancillary bore and the support structure positioned on top of the tooth root;
- inserting the post into the axial aperture in the support structure;
- adjusting the post through the support structure until it bottoms into the central bore;
- securing the position of the post with respect to the support platform, and
- casting a core and post using the prefabricated assembly.

24. The method as in claim 23, wherein the prefabricated assembly comprises a burnout core and post, and said cast core and post are formed using a lost wax process in a direct technique.

25. The method as in claim 23, wherein the prefabricated assembly is an impression post and comprising the steps of applying impression material to form an impression tray including the prefabricated assembly positioned therein and forming said cast core and post using indirect fabrication techniques.

* * * * *